United States Patent [19]
Weinberger et al.

[11] 3,947,128
[45] Mar. 30, 1976

[54] PATTERN COMPARISON
[76] Inventors: Zvi Weinberger, 24 Yehoshua Bin Nun; Avram Kalisky, 26 Hahagana St., both of Jerusalem, Israel
[22] Filed: Apr. 19, 1974
[21] Appl. No.: 462,303

[52] U.S. Cl............. 356/71; 340/146.3 E; 356/168
[51] Int. Cl.² ....................................... G06K 9/00
[58] Field of Search ...... 356/71, 165, 168; 250/556; 340/146.3 E

[56]     References Cited
       UNITED STATES PATENTS
2,646,717   7/1953   Selgin............................ 356/71 UX
3,511,571   5/1970   Ogle ............................ 340/146.3 E
3,619,060   11/1971  Johnson......................... 356/168 X OTHER PUBLICATIONS
Rosell, "Prism Scanner", Journal of the Opticall Society of America, Vol. 50, No. 6, pp. 521–526, June, 1960.

Primary Examiner—Alfred E. Smith
Assistant Examiner—Matthew W. Koren
Attorney, Agent, or Firm—Weingarten, Maxham & Schurgin

[57]           ABSTRACT
A method and device for the comparison of patterns, and especially of fingerprints, making possible the identification of a given person. The device comprises means for projecting an incoherent image of the finger to be compared onto a permanent fingerprint record, oscillating same with respect to each other, projecting the resulting image onto a photocell and ascertaining the A.C.-current characteristics of the resulting electrical signal. When the finger is positioned exactly, oscillation in one direction is adequate, if not oscillations in at least two directions are to be resorted to. The image of the finger is advantageously obtained by frustrated total reflection on the totally reflecting face of a prism. The permanent record and the image may be subjected to a predetermined distortion and/or magnification according to a predetermined code, reducing the risk of forgeries.

16 Claims, 3 Drawing Figures

Virtual image of finger

PATTERN COMPARISON

BACKGROUND OF THE INVENTION

During recent years many improvements have been made in the visual comparison of ink-recordings of fingerprints. Various optical methods have been resorted to in order to substantially reduce the tedious and time-consuming visual and manual classification and identification procedure. There has been described a coherent optical processor fingerprint identification apparatus in which identification is established by correlating an optical beam pattern representative of the finger to be identified with a prerecorded Fourier transform spatial filter of the fingerprint. In this known method use is made of a coherent light beam, and this is used for holographic and non-holographic systems of fingerprint comparison. According to the present invention non-coherent light is used, and this has a number of advantages, such as less expensive equipment needed, and a lesser degree of accuracy need during the initial recording of the fingerprint. Holographic systems require the use of transparencies for the holographic filter, whereas according to the present invention opaque reflective records can be used, as well as transparent ones.

SUMMARY OF THE PRESENT INVENTION

A method and device for the comparison of patterns, and especially of fingerprints, making possible the identification of a given person. The device comprises means for projecting an incoherent image of the finger to be compared onto a permanent fingerprint record, oscillating same with respect to each other in one direction; or in two directions at different frequencies; projecting the resulting image onto a photocell and ascertaining the A.C.-current characteristics of the resulting electrical signal. The image of the finger is advantageously obtained by frustrated total reflection on the totally reflecting face of a prism. The permanent record and the image may be subjected to keystone distortion according to a predetermined code, reducing the risk of forgeries.

The present invention relates to a novel device for the comparison of patterns making possible the positive identification of a given person. The invention relates specifically to the comparison of fingerprints, but modifications thereof can also be used for the comparison of photographs etc. The invention further relates to a novel process of fingerprint identification. A preferred device according to the present invention is adapted to ascertain whether a recorded fingerprint is identical with the fingerprint of the person identified by a document bearing such fingerprint record. The invention further relates to means of modifying identification patterns, such as fingerprints in a predetermined manner, so as to reduce the danger of fraudulent falsifications and misuses of documents bearing fingerprint records. The use of the novel device is apt to deter potential fradulent uses. The term document in this context includes identification papers, credit cards, and the like. Other and further features of the present invention will become apparent hereinafter.

The invention will be described in the following with reference to fingerprint identification, but it ought to be understood that it is not restricted thereto and that modifications thereof can be used for the identification of other patterns and of photographs. The widespread use of credit cards has resulted in various fradulent schemes. Cards can be stolen or forged and safety means used hitherto have not been adequate to prevent frauds and resulting losses due to such fradulent uses.

In the following the term "fingerprint" will be used for the specific pattern of ridges and valleys of the finger of the person which is being identified, whereas the term "fingerprint record" refers to a permanent record of such fingerprint, like the conventional record obtained by applying ink to the finger and pressing the same against a recording medium or by photographing the finger. The fingerprint record is obtained by using the device according to the invention. In this case either the positive or the negative may be used. The term also refers to transparencies, and these will be dealt with specifically hereinafter.

The device according to the present invention comprises an optical system for projecting an incoherent image of the finger to be compared onto a permanent fingerprint record, means for moving said projected fingerprint pattern respective the fingerprint record, and means for ascertaining the identity of these. According to a preferred embodiment of the invention, the fingerprint pattern projected onto the permanent fingerprint record is oscillated in two different directions, preferably at right angles with each other, one of these movements being at a slow rate of oscillation, the other at a rapid rate, and the resulting image is projected onto a photocell and the alternating-current nature of the resulting signal is determined. The term "slow rate of oscillation" designates a rate of about one-half to 10 oscillations per second in the one direction; the term "rapid oscillation" defines an oscillation of about 20 to 400 oscillations per second. Preferred frequencies of oscillations are 3 to 5 in the one, and 50 to 200 in the other direction.

The pattern resulting from the superpositioned fingerprint projection and fingerprint record is projected onto a photocell, and the nature of the electrical output of this photocell is determined. If the image of the fingerprint is identical with or very similar to the permanent fingerprint record, the A.C. signal coming from the photocell will be comparatively large, its frequency being that of the more rapid one of the periodic motions. When the two prints are in perfect register with each other, the permanent record being a positive, the D.C. signal will have a maximum, and when the record is a photographic negative, it will have a minimum. In both of these two cases, the oscillation of the fingerprint patterns with respect to each other results in an A.C. signal. It is clear that the oscillations can be obtained by a periodic movement of certain components of the optical system.

The optical system used for projecting an incoherent beam of light encoded with the fingerprint information onto the fingerprint record advantageously comprises a prism. The finger which is to be examined as to the correlation of its fingerprint is pressed against the totally reflecting face of this prism and an incoherent lightbeam is directed through one of the other faces of the prism. Without the finger pressed against the totally reflecting face of the prism, the beam undergoes total reflection. In the presence of the finger pressed against the totally reflecting face, light reflection is frustrated at the locations of the ridges of the fingerprints, while at the locations of the valleys of the fingerprint the total reflection takes place. Thus the beam of incoherent light is encoded with the fingerprint information, and this beam is projected onto the permanent fingerprint record. When a modified or distorted fingerprint record is used, the encoded beam is subjected to a similar modification so as to coincide with the permanent record. Details will be illustrated hereinafter.

It is possible to resort to a phase-contrast method, taking advantage of the large phase difference between the ridge reflections and the reflection from the totally reflecting face of the prism, which need not be total for phase contrast detection.

BRIEF DESCRIPTION OF THE DRAWINGS

The invention will be described in the following by way of illustration only with reference to the following schematical drawings, in which.

DESCRIPTION OF THE PREFERRED EMBODIMENT

Figure 1:
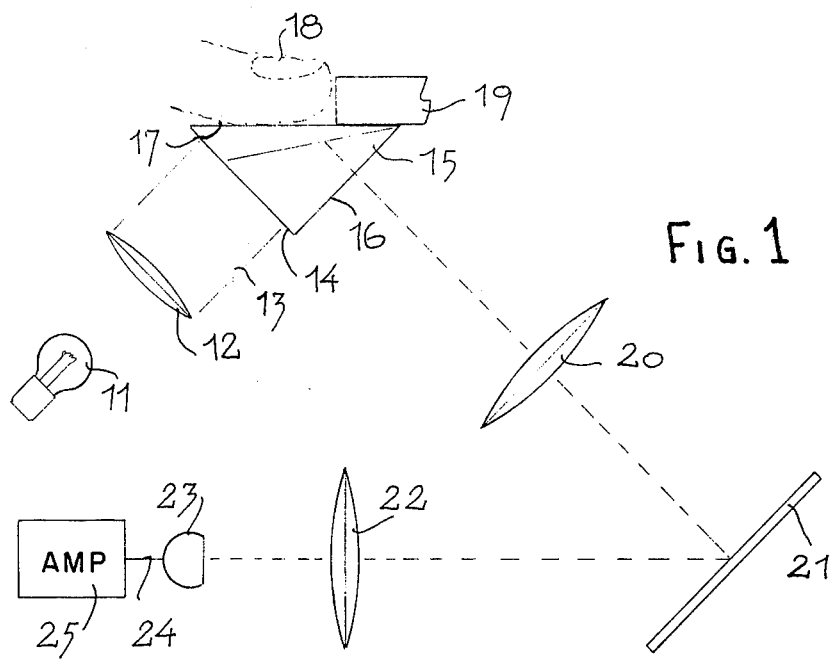
FIG. 1 is a schematical side-view of a device according to the invention.

As shown in FIG. 1, the fingerprint identification device according to the invention comprises in combination a source of light 11, a lens 12 which directs the parallel light-beam 13 through the surface 14 of the prism 15, and emerges through the surface 16 of said prism, after undergoing total reflection at the totally reflecting face 17 of the prism. The finger 18 to be examined as to the identity of its fingerprint with the permanent fingerprint record is pressed against the totally reflecting face 17, its position being guided by the member 19 attached to the prism. The guide member 19 establishes the position of the finger 18 within narrow predetermined limits, preferably of less than 2 mm. At the exact locations where the ridges of the fingerprint are in contact with the totally reflecting face 17 of prism 15 the total reflection of the lightbeam 13 is frustrated. Less light is reflected at the location of the ridges of the fingerprint and there exists also a significant phase difference in the light reflected from said ridges as compared with the totally reflected light, which corresponds to the valleys of the fingerprint.

The lightbeam leaving through surface 16 of the prism 15 passes through the lens (or lens-system) 20, and an image of the fingerprint of the finger 18 is projected onto the permanent fingerprint record 21. This may be negative or a positive of the fingerprint image. The dimensions and positions of the elements of the device are chosen in such manner that the projected image and the permanent record are of the same size. The image projected through lens 20 will substantially coincide with the permanent fingerprint record 21, and in order to compare these the superpositioned image and the permanent record are oscillated respective each other. When the finger is positioned exactly (which means within a displacement of less than about 1mm.), the oscillation need be effected in one direction only. The frequency of oscillation is preferably about 1-10 per second. When the position of the finger is such that the image of same is displaced to a certain extent (preferably less than about 2mm.) the superpositioned image and the permanent record are oscillated with respect to each other in at least two different directions. When these are oscillated in two different directions, this periodic motion is advantageously effected at a right angle with each other, and two different frequencies are chosen, one being comparatively slow, the other quite rapid. The order of magnitude of the motion in one direction can be from half to 10 oscillations per second, the other being from about 20 to 500, and preferably between 50 and 200 per second. The lightbeam bearing the fingerprint image is reflected from the permanent fingerprint record 21 through lens 22 and focused by this lens onto photocell 23 connected via leads 24 to the amplifier 25. The oscillation of the image of the fingerprint with respect to to the fingerprint record 21 can be effected by means of oscillating the fingerprint record 21 at different frequencies at an angle to each other, preferably at a right angle for the two directions of periodic movement. This is effected by conventional mechanical means, and details are not shown in the schematic drawing.

The comparison of the fingerprint image encoded on the lightbeam 13 with the permanent fingerprint record 21 is based on the fact that if the prints are identical, the oscillation will result in an A.C. current being generated by the photocell 23, and the nature of the current and its characteristics can be ascertained by the amplifier 25. When the prints are substantially different, a blurred image results from the superposition, and an ill-defined A.C. current will be obtained.

When the two prints are identical and when they coincide, the permanent print being a positive, there will be obtained a instantaneous signal of maximum intensity, and when the print is a negative the signal will be a minimum. In both of these cases the periodic movement of the image with respective to the permanent record results in an A.C. signal.

It is clear that the relative periodic movement may be attained by periodically moving the permanent record 21, but this may also be effected by a plurality of other means. Thus it is possible to oscillate members of the optical system. This may also be effected by means of rotating wedge prisms as described by F. A. Rosell; J. Opt. Soc. America, 50 (1960) 521-6 or by means of oscillating mirrors interposed in the optical path of the lightbeam directed at the permanent fingerprint.

To remove the necessity for a guide to restrict the angular position of the fingerprint, it is also possible to rotate the fingerprint image and the permanent record with respect to each other. It is necessary that the combination of linear and rotational motion thoroughly scan the fingerprint image with respect to the permanent record and that one of the periodic motions is sufficiently rapid so as to generate a periodic signal in the photocell. It is immaterial which of the frequencies is associated with the linear and which with the rotational scan.

It is possible to use a combination of two linear and one rotational motion; it is also possble to use a combination of a rotation motion and a linear motion in one direction only. It will be appreciated that the rotational scan need be effected over a few degrees of angle only.

It is clear that instead of the opaque fingerprint record 21 there may be used a transparency of such fingerprint record. In this case the light transmitted through the transparency will be collected by a lens located behind the transparency and projected onto the photocell 23. The evaluation of the results in this case is identical with that described above.

Instead of the prism 15, there may be used a dove prism (inverting prism), and also in this case the light entering through one of the sides of the prism is refracted to the top surface from which it is normally totally reflected and leaves through the other side. When the finger is pressed onto the upper surface of the dove prism, the light reflection is partially frustrated, resulting in a lightbeam encoded with the fingerprint information.

When the phase contrast method is to be used, there is used a polarizing filter located after lens 12 and phase contrast optics are located in place of the lens 20. As these are conventional means, they need not be described in detail.

The amplifier 25 is advantageously a tuned amplifier, and this is adjusted to a certain threshold of identification. Commercially available amplifiers such as Phase Sensitive Amplifiers or Phase and Frequency Sensitive Amplifiers, produced for examaple by Princeton Applied Research Inc. are suitable. The threshold adjustment is advantageously set in such manner that it will give a positive identification signal even in cases without a perfect match or absolute identity. It is adequate if the similarity is a very close one, and thus allowance is made for minor distortions or misaligment of the fingerprints which are compared. By adjusting the degree of similarity required for a positive identification it is possible to eliminate fraud by the use of fingerprints having a low degree of similarity, yet to avoid mistakes and unpleasant situations due to the imperfect match of an authentic record and the fingerprint image of its owner. The threshold may be adjusted according to the degree of security required and the amount of unpleasantness one is willing to cause.

Figure 2:
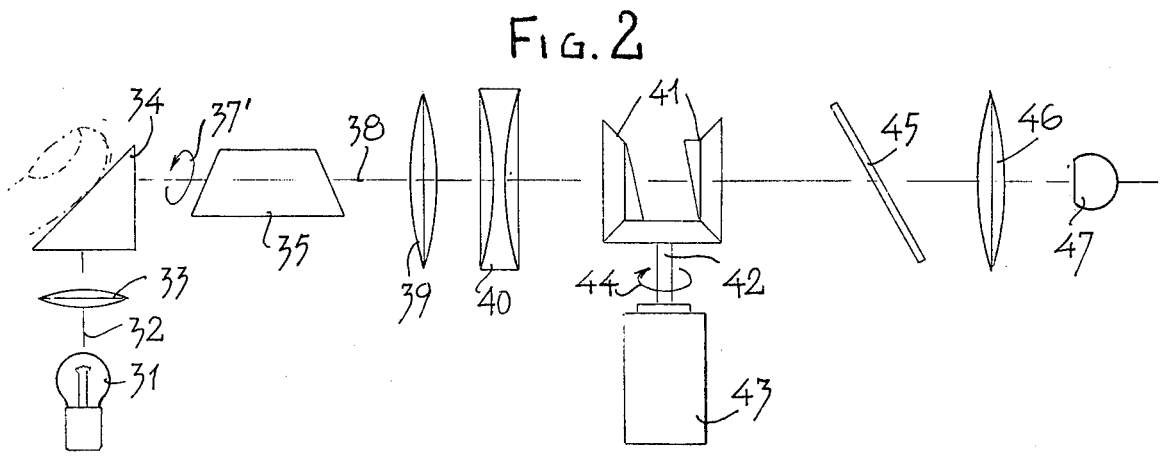
FIG. 2 is a schematic illustration of another device according to the invention.

FIG. 2 illustrates in a schematic manner a different embodiment of a device according to the present invention. The beam of incoherent light 32 from light source 31 passes through lens 33 and the parallel beam enters through one side of the prism 34 and leaves through the other side, the finger pressed against the totally reflecting face of prism 34 resulting in a frustration of the total reflection along the ridges of the fingerprint. The beam emerging from the prism passes through the dove prism 35 which is rotated around the optical axis 38 as shown by the arrow 37', and passes after passage through the dove prism through the zoom lens 39–40. As the dove prism is rotated about the direction of the lightbeam, the individual rays rotate around each other with twice the angular velocity of the prism. After the passage through the dove prism and the zoom lens, the light beam passes through the rotating wedge-prism system 41 which is rotated about the axis 42, actuated by motor 43 as indicated by the arrow 44. The beam passing through the rotating wedge-prism system undergoes an upward and downward displacement resulting in a two-dimensional scanning of the permanent fingerprint record 45 which is a transparency. The zoom lens makes possible to adjust the relative size of the projected image of the fingerprint and of the permanent fingerprint record. The rotation of the dove prism is effected at a frequency of about one-half to 10 about the optical axis.

The superpositioned images are projected by lens 46 onto the photocell 47 which is connected with means for ascertaining the nature of the resulting current, adapted to determine the degree of correspondence of the fingerprint which is being examined with the permanent fingerprint record.

In order to prevent forgeries and the exchange of cards by persons having similar fingerprints, it is possible to include in the permanent record or in the card bearing such record additional means of identification, such as a magnetic code or the like. It is furthermore possible to modify the permanent fingerprint according to a predetermined scheme. For example, the size of the record may be magnified or made smaller by a predetermined factor depending on the code, which can be according to the name or some other parameter. This change of size is easily accomplished, and the projection of the fingerprint onto such record will be according to the same code.

Figure 3:
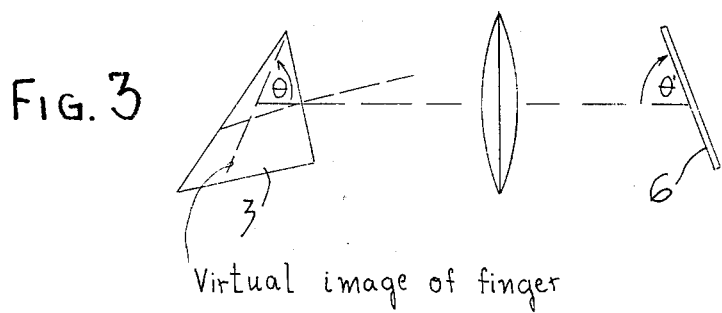
FIG. 3 is an illustration of the relation between the angles of the light beam and the angle of the fingerprint record with said beam.

A predetermined distortion may be resorted to as is illustrated with respect to FIG. 3. If the virtual image of the fingerprint through the prism 3 makes an angle $\theta$ with the optical axis, then the card 6 bearing the permanent record must make an angle $\theta'$ with the optical axis in order that the image projected be in focus. The relation of $\theta$ to $\theta'$ is:

$$\tan \theta' = \frac{1}{M} \cdot \tan \theta$$

where $M$ is the magnification of the optical system. By changing the magnification and the angle of the optical axis and the angle of the image card in accordance with the above relation, different amounts of key-stone distortion and/or magnification are introduced.

What is claimed is:

1. A device for the comparison of the image of a given member and of a permanent record of said member, comprising in combination an optical modification in the permanent record of said member, the optically modified record including a predetermined significantly distorted geometrically dissimilar image of said member, means for projecting an image of said member onto the optically modified permanent record of said member and including means for providing a corresponding optical modification in the projected image, means for oscillating said record with respect to said projected image, means for projecting the image resulting from the oscillation of said record with respect to said projected image onto a photoelectric device and means for detecting a predetermined A.C. fluctuation in the electric current from said photoelectric device.

2. A device according to claim 1, wherein the oscillation is in two different directions.

3. A device according to claim 1, for the comparison of the image of a finger with a fingerprint record, comprising an optical element having reflective interior faces, said permanent record being said fingerprint record, means for forming a beam of light and for projecting said beam of light onto said optical element wherein said beam of light undergoes reflection at one of the faces of said optical element, means for positioning the finger in a predetemined position on said reflecting face of the optical element, said projecting means including means for projecting the reflected beam of light onto said permeanent record, said means for oscillating the permanent record with respect to the projected image providing oscillation at a predetermined frequency.

4. A device according to claim 3 wherein the optical element is one wherein the beam undergoes total reflection on the face on which the finger is positioned.

5. A device according to claim 3, wherein said oscillating means includes means for oscillating the reflected beam with respect to the permanent record in two different directions at predetermined frequencies.

6. A device as claimed in claim 3, wherein the optical element is a prism.

7. A device as claimed in claim 3, wherein the photoelectric device is a photocell.

8. A device according to claim 3, wherein the means for forming the beam of light is a source of incoherent light.

9. A device according to claim 1, wherein the oscillating means is a rotating dove prism.

10. A device according to claim 1, wherein the oscillating means is a rotating wedge prism.

11. A device according to claim 1, wherein the means for providing an indications of a predetermined A.C. fluctuation is a phase sensitive amplifier.

12. A device as claimed in claim 1 wherein said image projecting means includes phase contrast optics and means are provided to illuminate said member with polarized light.

13. A device for comparing a fingerprint image with a fingerprint record, comprising means for forming a beam of light, an optical element, means for projecting said beam of light onto said optical element for reflection from a surface thereof against which a finger is to be pressed, means for positioning the finger in a predetermined position with respect to the optical element, a permanent fingerprint record having a predetermined optical modification, the optically modified record including a predetermined, significantly distorted, geometrically dissimilar image of a fingerprint, phase-contrast optics means for projecting the image of the finger in the reflected beam of light onto said permanent fingerprint record with a predetermined further optical modification similar to the optical modification in said record, means for oscillating the permanent fingerprint record with respect to the image projected onto it, means for projecting the resulting image onto a photoelectric element, and means for detecting a predetermined A.C. fluctuation in the electrical current from said photoelectric element.

14. A method for comparing the image of a given member with an optical modification in a permanent record of said member, the optically modified permanent record including a predetermined, significantly distorted, geometrically dissimilar image of said member, comprising the steps of projecting a similar optical modification of an image of said member onto the optically modified permanent record of said member, oscillating said projected image with respect to said permanent record, projecting the resulting image onto a photoelectric element and detecting a predetermined fluctuation in the electric current from said photoelectric element.

15. A method as claimed in claim 14, wherein the oscillation is in two directions perpendicular with respect to each other, the one at a frequency of from one-half to 10 oscillations per second, the other at a frequency of from 20 to 400 oscillations per second.

16. A method according to claim 15, for the comparison of a fingerprint with a fingerprint record, wherein the image projecting step includes the step of pressing a finger against the face of an optical element projecting a light beam onto said surface so as to result in a frustrated reflection from said surface, and projecting the frustrated reflection onto the optically modified permanent record.

* * * * *